United States Patent
Moazen et al.

(10) Patent No.: US 9,623,256 B2
(45) Date of Patent: Apr. 18, 2017

(54) METHOD OF FABRICATING AND TESTING A CIRCUIT BOARD

(71) Applicant: Boston Scientific Neuromodulation Corporation, Valencia, CA (US)

(72) Inventors: Damon Moazen, Northridge, CA (US); Robert G. Lamont, Van Nuys, CA (US); Robert R. Tong, Valencia, CA (US); Navin N. Bunyan, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/000,146

(22) Filed: Jan. 19, 2016

(65) Prior Publication Data
US 2016/0129268 A1 May 12, 2016

Related U.S. Application Data

(62) Division of application No. 14/525,941, filed on Oct. 28, 2014, now Pat. No. 9,265,947.
(Continued)

(51) Int. Cl.
| | |
|---|---|
| *A61N 1/372* | (2006.01) |
| *A61N 1/375* | (2006.01) |
| *A61N 1/36* | (2006.01) |
| *H05K 3/30* | (2006.01) |
| *H05K 1/02* | (2006.01) |
| *H05K 1/11* | (2006.01) |

(52) U.S. Cl.
CPC ....... *A61N 1/3758* (2013.01); *A61N 1/36125* (2013.01); *H05K 1/0268* (2013.01);
(Continued)

(58) Field of Classification Search
CPC ............ A61N 1/36125; A61N 1/37229; A61N 1/37658; H05K 1/0268; H05K 1/117;
(Continued)

(56) References Cited

U.S. PATENT DOCUMENTS

| | | | | |
|---|---|---|---|---|
| 4,647,133 | A * | 3/1987 | Renken | H05K 3/328 29/860 |
| 6,057,175 | A * | 5/2000 | Milla | A61N 1/05 257/E23.125 |

(Continued)

FOREIGN PATENT DOCUMENTS

| | | |
|---|---|---|
| JP | 04-121772 U | 10/1992 |
| WO | 2013/077468 | 5/2013 |

OTHER PUBLICATIONS

International Search Report and Written Opinion regarding corresponding PCT Application No. PCT/US2014/062923, dated Feb. 10, 2015.

*Primary Examiner* — Carl Arbes
(74) *Attorney, Agent, or Firm* — Lewis, Reese & Nesmith, PLLC

(57) ABSTRACT

Designs and methods of construction for a printed circuit board (PCB) in an implantable pulse generator (IPG) are disclosed which facilitate IPG PCB testing while also providing for protection of IPG circuitry in a simple and cost effective manner. The IPG PCB is formed as part of a larger test PCB, which includes an extender portion with traces routing nodes of interest in the IPG PCB to an edge connector. IPG electronics are mounted or soldered to the IPG PCB, and then such electronics are tested via the edge connector. The IPG PCB is then singulated from the extender portion in a manner leaving one or more PCB tabs at the severed edge of the PCB. The PCB tab(s) extend from the severed edge, and create an offset distance preventing traces severed and now exposed at the severed edge from contacting and potentially shorting to conductive structures in the IPG.

20 Claims, 9 Drawing Sheets

Related U.S. Application Data

(60) Provisional application No. 61/902,062, filed on Nov. 8, 2013.

(52) U.S. Cl.
CPC .............. H05K 1/117 (2013.01); H05K 3/30 (2013.01); *A61N 1/37229* (2013.01); *H05K 2201/09145* (2013.01); *H05K 2203/162* (2013.01); *Y10T 29/49004* (2015.01)

(58) Field of Classification Search
CPC ........... H05K 3/30; H05K 2201/09145; H05K 2203/162; Y10T 29/49004
See application file for complete search history.

(56) References Cited

U.S. PATENT DOCUMENTS

| | | | |
|---|---|---|---|
| 6,109,934 A | 8/2000 | Madsen et al. | |
| 6,245,092 B1 * | 6/2001 | Schaldach, Jr. | ........ H05K 1/118 607/1 |
| 6,516,227 B1 | 2/2003 | Meadows et al. | |
| 6,567,703 B1 | 5/2003 | Thompson et al. | |
| 6,991,961 B2 * | 1/2006 | Hubbard | ............. H01L 23/4985 257/786 |
| 8,433,404 B2 * | 4/2013 | Chavan | ................ A61N 1/3956 607/4 |
| 2003/0144707 A1 | 7/2003 | Ruben et al. | |
| 2004/0235326 A1 | 11/2004 | Reisinger et al. | |
| 2005/0241848 A1 | 11/2005 | Michaud et al. | |
| 2006/0122658 A1 | 6/2006 | Kronich et al. | |
| 2007/0109729 A1 | 5/2007 | Fujii et al. | |
| 2010/0256696 A1 | 10/2010 | Schleicher et al. | |
| 2010/0298897 A1 * | 11/2010 | Chavan | ................ H03K 17/567 607/5 |
| 2013/0206472 A1 | 8/2013 | Stevenson et al. | |
| 2015/0066114 A1 | 3/2015 | Bunyan et al. | |
| 2015/0134036 A1 * | 5/2015 | Moazen | ............. A61N 1/36125 607/116 |

* cited by examiner

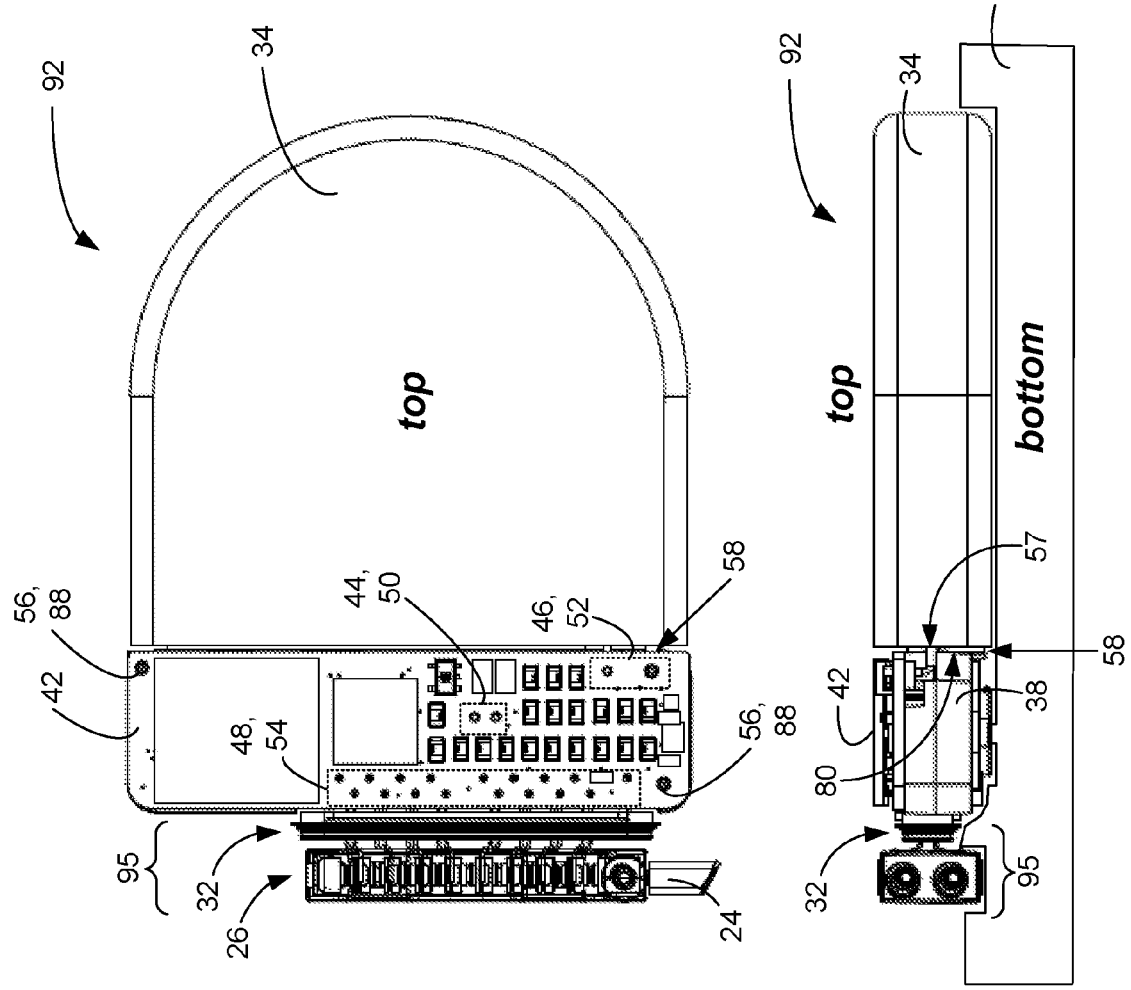
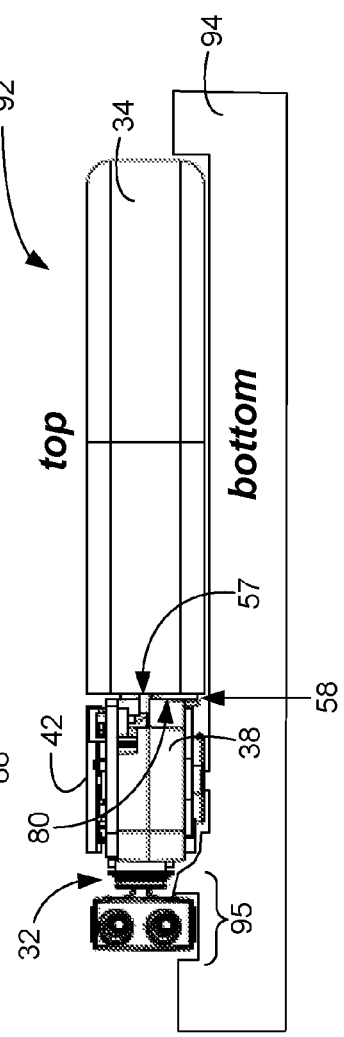

METHOD OF FABRICATING AND TESTING A CIRCUIT BOARD

CROSS REFERENCE TO RELATED APPLICATIONS

This application is a divisional of U.S. patent application Ser. No. 14/525,941, filed Oct. 28, 2014, which is a non-provisional of U.S. Provisional Patent Application Ser. No. 61/902,062, filed Nov. 8, 2013. Priority is claimed to these applications and each application is incorporated herein by reference in its entirety.

FIELD OF THE INVENTION

The present invention relates to implantable medical devices, and more particularly to an improved design and method of construction and testing of a circuit board for an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

An SCS system typically includes an Implantable Pulse Generator (IPG), whose structure and construction is further described in U.S. Provisional Patent Application No. 61/874,194, entitled "Construction for an Implantable Medical Device Employing an Internal Support Structure," filed Sep. 5, 2013, which is incorporated herein by reference in its entirety. The IPG 10 of the '194 Application is shown in FIG. 1, which includes a biocompatible device case 30 that holds the circuitry and battery 34 (FIG. 2) necessary for the IPG to function. The IPG 10 is coupled to electrodes 16 via one or more electrode leads 14 that form an electrode array 12. The electrodes 16 are carried on a flexible body 18, which also houses the individual signal wires 20 coupled to each electrode 16. The signal wires 20 are also coupled to proximal contacts 22, which are insertable into lead connectors 24 fixed in a header 28 on the IPG 10, which header can comprise an epoxy for example. Once inserted, the proximal contacts 22 connect to header contacts 26 in the lead connectors 24, which header contacts 26 are in turn coupled by feedthrough pins 48 to circuitry within the case 30 as will be explained subsequently. In the illustrated embodiment, there are sixteen electrodes 16 (E1-E16) split between two leads 14, although the number of leads and electrodes is application specific and therefore can vary. In a SCS application, electrode leads 14 are typically implanted on the right and left side of the dura within the patient's spinal cord. The proximal electrodes are then tunneled through the patient's tissue to a distant location, such as the buttocks, where the IPG case 30 is implanted, at which point they are coupled to the lead connectors 24.

FIG. 2 shows perspective bottom and top sides of the IPG 10 with the case 30 removed so that internal components can be seen. In particular, a battery 34, communication coil 40, and a printed circuit board (PCB) 42, can be seen. As explained in the '194 Application, these components are affixed to and integrated using a rigid (e.g., plastic) support structure 38. Battery 34 in this example is a permanent, non-wirelessly-rechargeable battery. (Battery 34 could also be rechargeable, in which case either coil 40 or another recharging coil would be used to wirelessly receive a charging field that is rectified to charge the battery 34). The communication coil 40 enables communication between the IPG 10 and a device external to the patient (not shown), thus allowing bidirectional communication to occur by magnetic induction. The ends of coil 40 are soldered to coil pins 44 molded into the support structure 38 to facilitate the coil 40's eventual connection to circuitry on the IPG PCB 42. IPG PCB 42 integrates the various circuits and electronics needed for operation of the IPG 10. As shown in FIG. 2, coil 40 is proximate to the bottom side of the support structure 38 and case 30, while the IPG PCB 42 is proximate to the top side.

FIG. 3 shows a lead connector subassembly 95 for the IPG 10, which includes the lead connectors 24, the header contacts 26, feedthrough pins 48, and a feedthrough 32. The feedthrough 32 acts as a hermetic means for passing via the feedthrough pins 48 electrode signals between the header contacts 26 (and ultimately electrodes 16) and the circuitry internal to the case 30 on the IPG PCB 42. Lead connector subassembly 95 can be formed by slipping the feedthrough pins 48 through the feedthrough 32, soldering one end of the feedthrough pins 48 to appropriate header contacts 26 in the lead connectors 24, and soldering or brazing the feedthrough pins 48 in the feedthrough 32 in a hermetic manner. Notice that the free ends of the feedthrough pins 48 are bent at 90 degrees relative to the feedthrough 32, which facilitates connection to the IPG PCB 42 as discussed subsequently. In this example, there are two rows of bent feedthrough pins 48, with the top row spaced by a distance d1, and the bottom row spaced by a distance d2, from a bottom surface of the feedthrough 32, the relevance of which will be explained later.

Some of the construction steps of the IPG 10 are shown in FIGS. 4A and 4B, and because these steps are disclosed in the '194 Application, they are only briefly summarized here. Construction begins by affixing a battery terminal face 57 of the battery 34 to the support structure 38, using double sided tape 58 for example. The combined support structure 38 and battery 34 is then placed in an assembly jig 94 as shown in cross section in FIG. 4B. Next, the lead connector subassembly 95 (FIG. 3) is positioned within the jig 94. Like the feedthrough pins 48 in the lead connector assembly 95, the battery terminals 46 are bent at 90 degrees relative to the battery terminal face 57, and so both the feedthrough pins 48 and battery terminals 46 are now pointing upward when placed in the jig 94. Next, the IPG PCB 42—preferably pre-fabricated with its electrical components—is affixed to the top side of the support structure 38. In this regard, IPG PCB 42 includes coil solder pin holes 50, battery terminal solder holes 52, feedthrough pin solder holes 54, and support structure mounting holes 56, which are respectively slipped over the upward-pointing coil pins 44 (in the support structure 38), feedthrough pins 48, battery terminals 46, and mounting pins 88 of the support structure 38. The coil pins 44, feedthrough pins 48, battery terminals 46 are then soldered to the coil solder pin holes 50, feedthrough pin solder holes 54, and battery terminal solder holes 52 respectively to electrically couple them to the IPG PCB 42. Thereafter, and as explained in the '194 Application, the resulting IPG subassembly 92 is then placed in its case 30, which is welded together and to the feedthrough 32, and the header 28 is then added to complete IPG 10's construction.

The inventors consider it desirable to electrically test the IPG PCB 42 before it is attached to the support structure 38 and electrically coupled to the battery 34 and feedthrough pins 48, and sealed within its case 30, and techniques are disclosed for doing so, which also involve improved designs and methods of constructing the IPG PCB 42.

BRIEF DESCRIPTION OF THE DRAWINGS

FIGS. 4A and 4B show certain steps in the assembly of the IPG in accordance with the prior art.

DETAILED DESCRIPTION

Designs and methods of construction for a printed circuit board (PCB) in an implantable pulse generator (IPG) are disclosed which facilitate IPG PCB testing while also providing for protection of IPG circuitry in a simple and cost effective manner. The IPG PCB is formed as part of a larger test PCB, which includes an extender portion with traces routing nodes of interest in the IPG PCB to an edge connector. IPG electronics are mounted or soldered to the IPG PCB, and then such electronics are tested via the edge connector. The IPG PCB is then singulated from the extender portion in a manner leaving one or more PCB tabs at the severed edge of the PCB. The PCB tab(s) extend from the severed edge, and create an offset distance preventing traces severed and now exposed at the severed edge from contacting and potentially shorting to conductive structures in the IPG, such as a feedthrough.

The inventors consider it desirable to electrically test the IPG PCB 42 before it is attached to the support structure 38 and electrically coupled to the battery 34 and feedthrough pins 48, and sealed within its case 30, as explained earlier (FIGS. 4A and 4B). Such testing can be difficult given the relatively small size of IPG PCB 42, which must fit inside the small case 30 of the IPG 10, and which must accommodate the primary battery 34. Even though difficult to test because of its size, such testing of the IPG PCB 42 at this stage is important, as its components can be easily damaged, particularly if the IPG PCB 42 is handled by assembly technicians.

Figure 5:
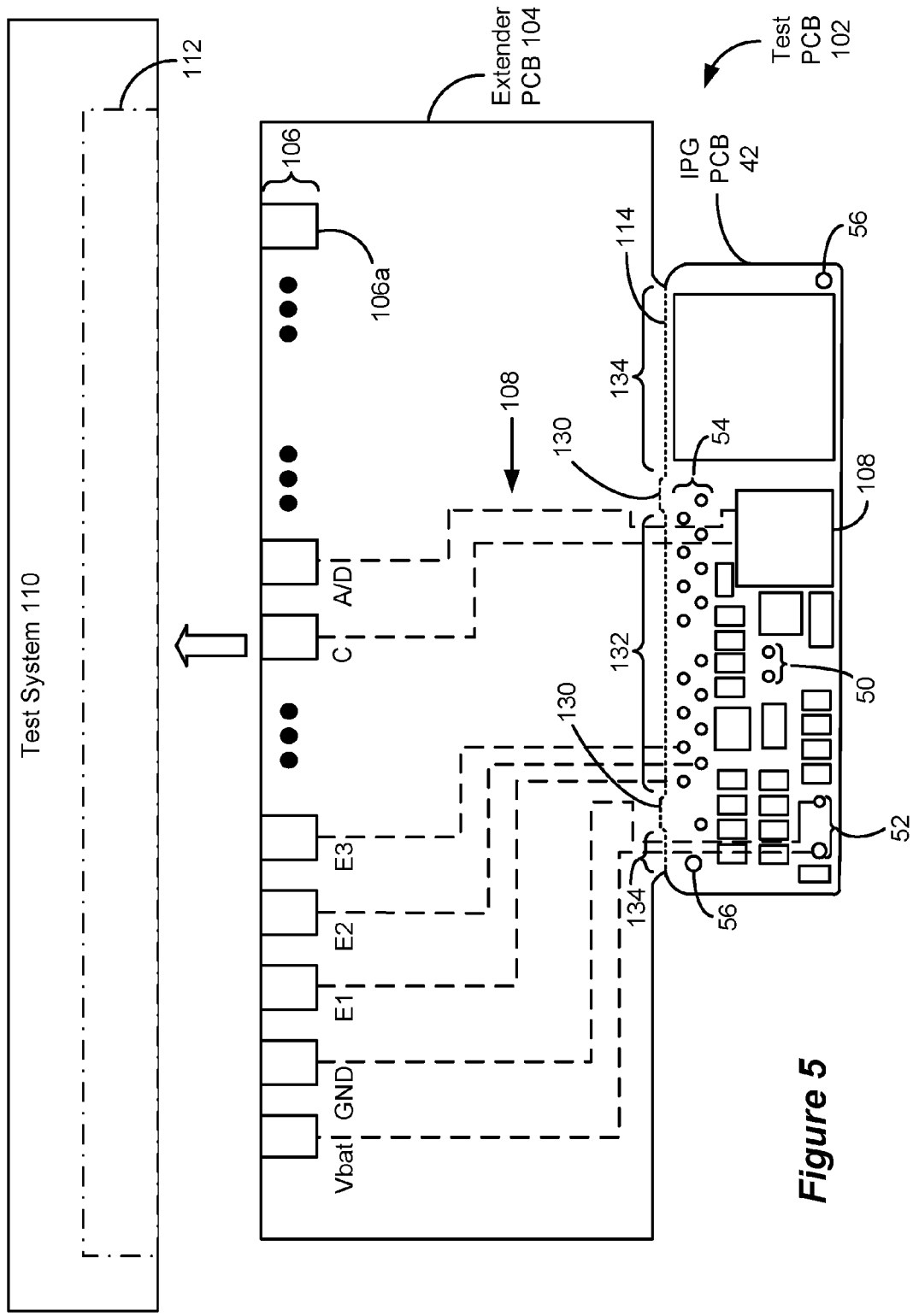
FIG. 5 shows an improved method of manufacturing and testing a printed circuit board (PCB) for use in the IPG, in which the IPG PCB is formed with an extender PCB portion that can interface with a test system.

FIG. 5 shows one means of fabricating the IPG PCB 42 in a manner to facilitate its testing prior to connection with other IPG components. As shown, the IPG PCB 42 is formed as part of a larger test PCB 102, which includes an extender PCB portion 104 having an edge connector 106 composed of contacts 106a coupled to various PCB traces 108. Traces 108 also couple to various nodes of interest in the IPG PCB portion 42 of the test PCB 102. The extender PCB 104 is preferably significantly larger in area than the size of the IPG PCB 42 (e.g., at least twice the area), and unlike the IPG PCB 42 has no electronic devices mounted to it, which facilitates easier handling of the IPG PCB 42 during testing, as an assembly technician can touch the extender PCB 104 without fear of damaging the electrical components otherwise mounted to the IPG PCB 42.

The edge connector 106's contacts 106a are of standard size and pitch to meet with corresponding contacts in an edge connector socket 112 coupled to a test system 110, which test system 110 can be of many different types used by a manufacturer. In one example, edge connector 106 and socket 112 comprise 80 pins, with 40 contacts 106a on the top and bottom of the extender PCB 104 (and in the socket 112), although not all of these pins would necessarily be used.

In one example, the test PCB 102, and hence the IPG PCB 42 and extender PCB 104, comprise a two-layer PCB in which two layers of conductive traces can be formed. However, this is not strictly necessary, and the numbers of layers needed in test PCB 102 will largely be dictated by the number of layers needed to interconnect the electrical components on IPG PCB 42. Additional layers needed by the IPG PCB 42, but not necessary to form traces 108 connecting the edge connector 106 with nodes of interest in the IPG PCB 42, may simply be unused in the extender PCB 104.

Thus, the electronic components needed to implement the functionality of the implantable medical device of the IPG PCB 42 (IPG 10) can be surface mounted or otherwise soldered to the IPG PCB 42 portion of the test PCB 102 in standard fashion, and then the edge connector 106 of the extender PCB 104 portion of the test PCB 102 can be inserted in the socket 112 associated with the test system 110 to test the IPG PCB 42 electronics.

As discussed above, nodes of interest in the IPG PCB 42 are routed via traces 108 to the edge connector 106 to allow such testing to occur. For example, the test system 110 can provide reference voltages to the nodes on IPG PCB 42 where the positive (Vbat) and negative (GND) battery terminals 46 will eventually be coupled, i.e., to battery terminal solder holes 52. As well as providing power to operate the IPG PCB 42 during the test, the test system 110 can also monitor the current drawn from node Vbat to verify whether significant leakage current is being drawn by the IPG PCB 42 indicative of a defect.

Traces 108 can also be connected to the electrode nodes (Ex) on the IPG PCB 42, i.e., to the feedthrough pin solder holes 54 to which the feedthrough pins 48 will eventually be connected, allowing these nodes to be coupled to the IPG electrodes 16. This is useful for example to allow the test system 110 to make sure the electrode electronics on IPG PCB 42 are not short or open circuited.

Other nodes of interest in the IPG PCB 42 may be routed via traces 108 as well, such as various bus signals on the IPG PCB 42 including control (C) and address/data (A/D) signals, which the tester can use to activate or monitor various modes of operation of the IPG PCB 42 circuitry. Other nodes of interest which may be routed include clock signals, other power supply or reference voltages, the nodes where the coil 40 will eventually be connected, i.e., to coil solder pin holes 50, etc. The signals shown in FIG. 5 are thus merely exemplary, and in an actual implementation many other nodes in IPG PCB 42 can be activated and/or monitored by the test system 110 via traces 108.

Note that the traces 108 can pass anywhere between the IPG PCB 42 and the extender PCB 104, except in the location of PCB tabs 130, whose function is explained further below. Preferably, the traces 108 pass through a portion 132 between the two PCB tabs 130 that are shown, but this is not strictly necessary, and some traces are shown passing through portions 134 on the outsides of the PCB tabs 130.

After electronic testing is completed, and if proper operation of the IPG PCB 42 is confirmed, the IPG PCB 42 is singulated from the PCB extender 104 along sever line 114, and the PCB extender 104 portion of test PCB 102 can then be disposed of In one example, a Computer Numerical Control (CNC) router or milling machine is used to cut (e.g., saw) the IPG PCB 42 from the extender PCB 104, with a Computer Aided Design (CAD) file used to guide the router's cutting element along sever line 114 so as to define the shape of the PCB tabs 130. Other methods of singulating the IPG PCB 42 may also be used, such as manual breaking, v-score shearing, nibbling, punching, etc. Note that while the sever line 114 may be perforated or scored on the test PCB 102, this is not strictly necessary, particularly if cutting is used for singulation.

Figure 6:
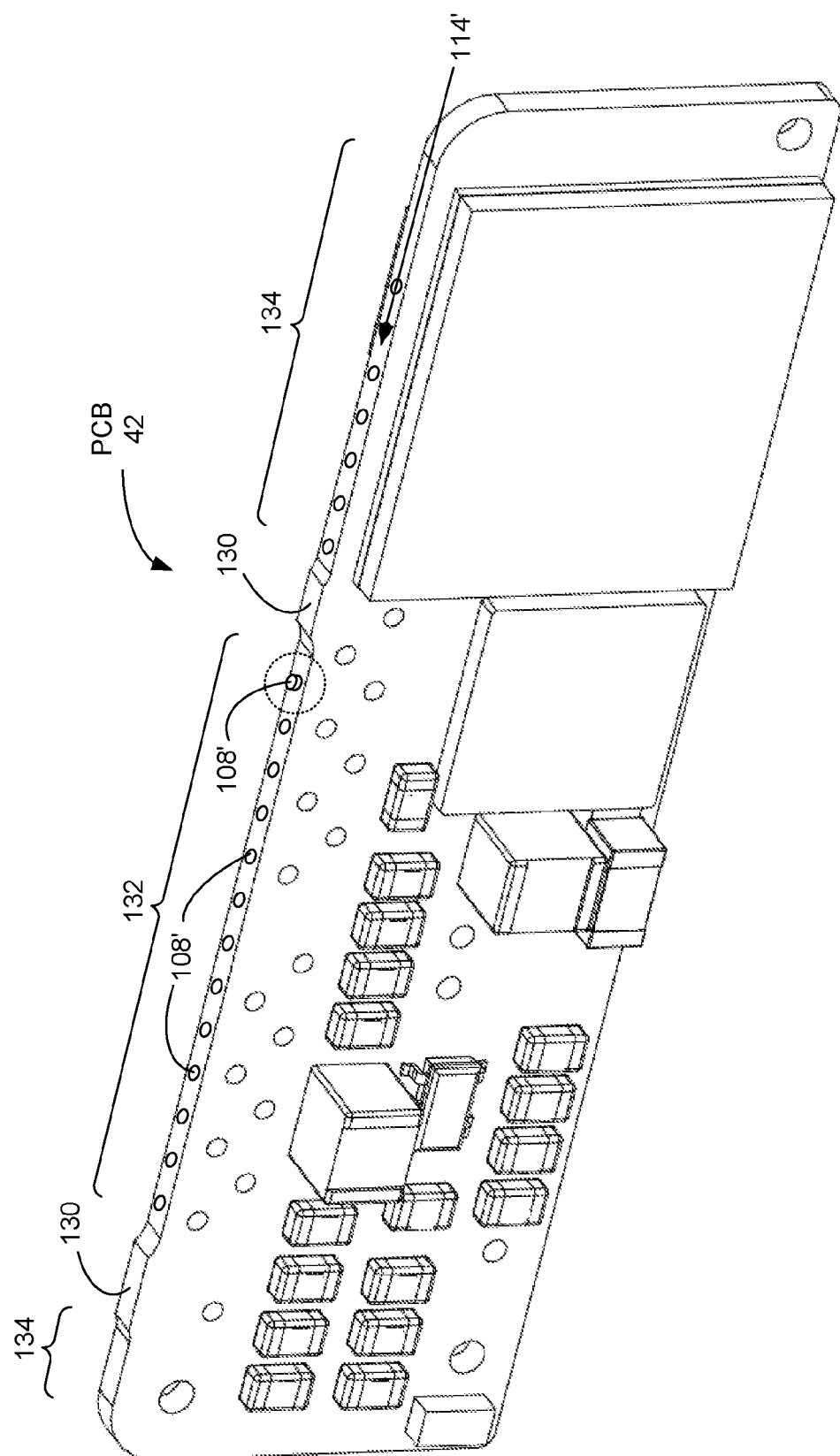
FIG. 6 shows the IPG PCB after testing and after it is severed from the extender PCB, and shows severed traces at its severed edge, and PCB tabs formed in the severed edge to prevent shorting of the severed traces.

FIG. 6 illustrates the IPG PCB 42 after singulation, and in particular shows sever line 114 in cross section, i.e., along the severed edge 114' of the IPG PCB 42. Because traces 108 cross sever line 114, they too will be severed by the singulation process, and thus are exposed (not insulated) in cross section 108' at severed edge 114'. (The severed traces 108' are exaggerated in size, and assume only a single level PCB 42). The severed traces 108' at the severed edge 114' of IPG PCB 42 are exposed, and thus could short circuitry connected to such nodes on the IPG PCB 42, particularly if sever line 114 is cut in a rough manner allowing a severed trace 108' to protrude from the severed edge 114', as shown in the dotted-lined circle.

Figure 7:
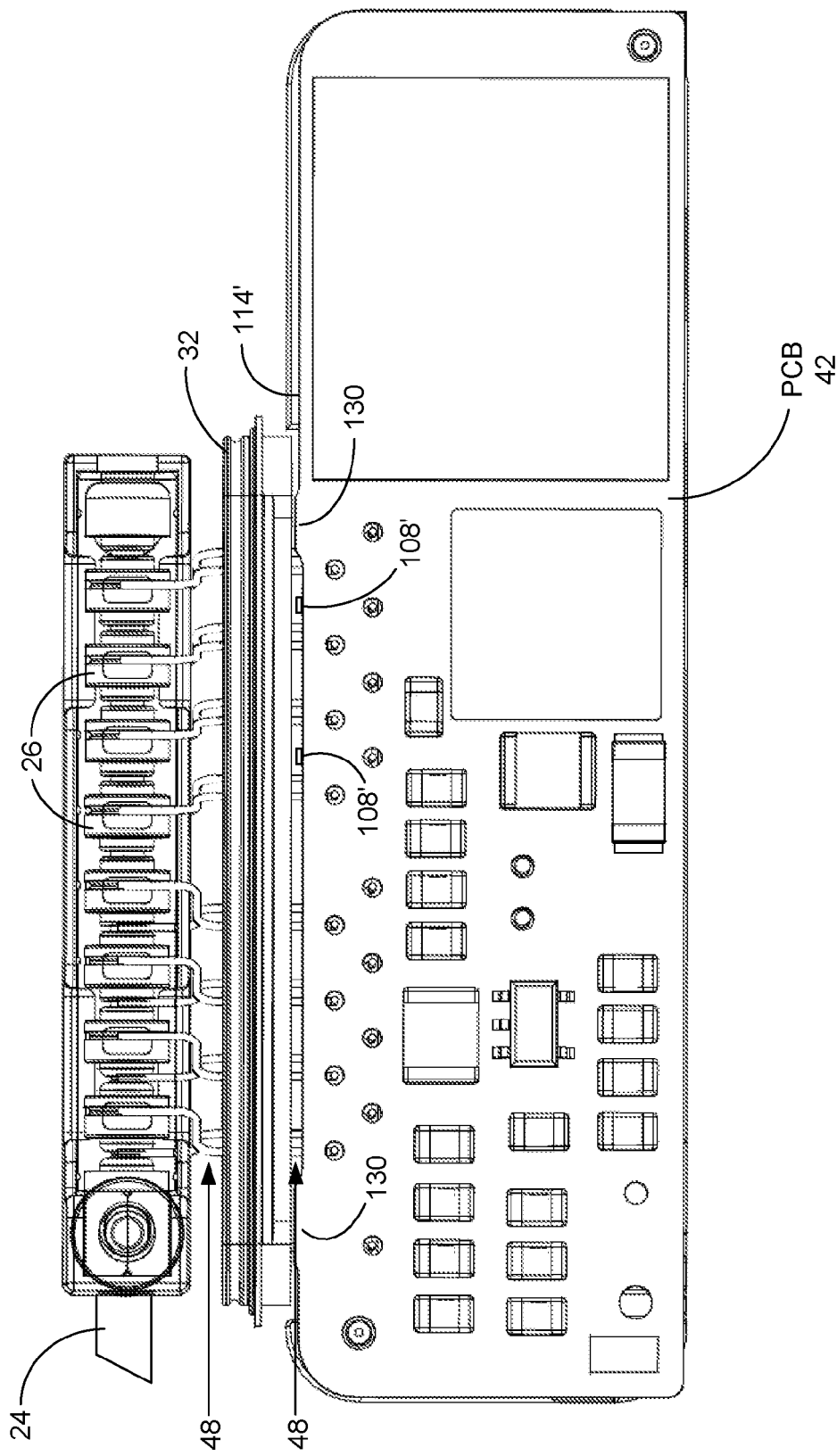
FIGS. 7 and 8 show the severed IPG PCB in relation to a feedthrough of the IPG, and shows how the PCB tabs prevent shorting of the severed traces to the feedthrough.

Shorting of the severed traces 108' is especially concerning for the design of IPG 10 given the proximity of severed edge 114' of IPG PCB 42 to the feedthrough 32, as shown in FIG. 7. Note that the plane of IPG PCB 42 is perpendicular to the bottom surface of the feedthrough 32, such that severed edge 114' of the IPG PCB 42 is parallel with, and close to, this surface. Because the feedthrough 32 is conductive and welded to the case 30, and because the case 30 is typically grounded by the IPG 10 (or at least set to a fixed potential, as it too can be used as an electrode 16), severed traces 108' that touch the feedthrough 32 could adversely affect the circuitry on IPG PCB 42 connected to such traces. Even if severed traces 108' do not touch the feedthrough 32 during manufacturing, they could do so later (even after implantation in a patient), especially considering that the IPG 10 is subject to mechanical shock and vibration and thermal expansion, which can cause the components in the IPG 10 to move with respect to each other. Additionally, unwanted conductive particulates within the IPG's case 30 could eventually lodge between the severed traces 108' and the feedthrough 32, causing a short.

While an insulator could be applied to the severed edge 114' to cover the severed traces 108', such as additional manufacturing step is not desired, as it would raise the risk of damaging the IPG PCB 42 or introducing new defects.

Instead, and in accordance with an aspect of the invention, at least one PCB tab 130 is provided along the severed edge 114' of the side of the IPG PCB 42, and two such tabs 130 are shown in FIG. 7. The PCB tab(s) 130 guarantee that an offset distance will maintained between the severed traces 108' and the feedthrough 32, which offset distance is designed to be significantly larger than the expected length of severed traces 108' protruding from the severed edge 114', and significantly larger than the size of any unwanted particulates that might be present in the IPG 10. Said differently, severed traces 108' at the severed edge 114' are recessed by the offset distance with respect to the PCB tab(s) 130, thus preventing the exposed severed traces 108' from contacting the feedthrough 32. Conveniently, and preferably, the shape of the PCB tab(s) 130 can be defined during the singulation process by designing the shape of sever line 114 accordingly.

Because the particular concern for IPG 10 is the shorting of severed traces 108' to the feedthrough 32, the PCB tabs 130 are located near to the ends of the feedthrough 32 along its length as shown in FIG. 7, although this is not strictly necessary. In other IPG designs, the location of the PCB tab(s) 130 along the severed edge 114' may change depending on the position of the components in the IPG, and in accordance with the isolation that is desired between the severed traces 108' and other conductive structures. One or more than two PCB tabs 130 may be provided along severed edge 114'.

Figure 1:
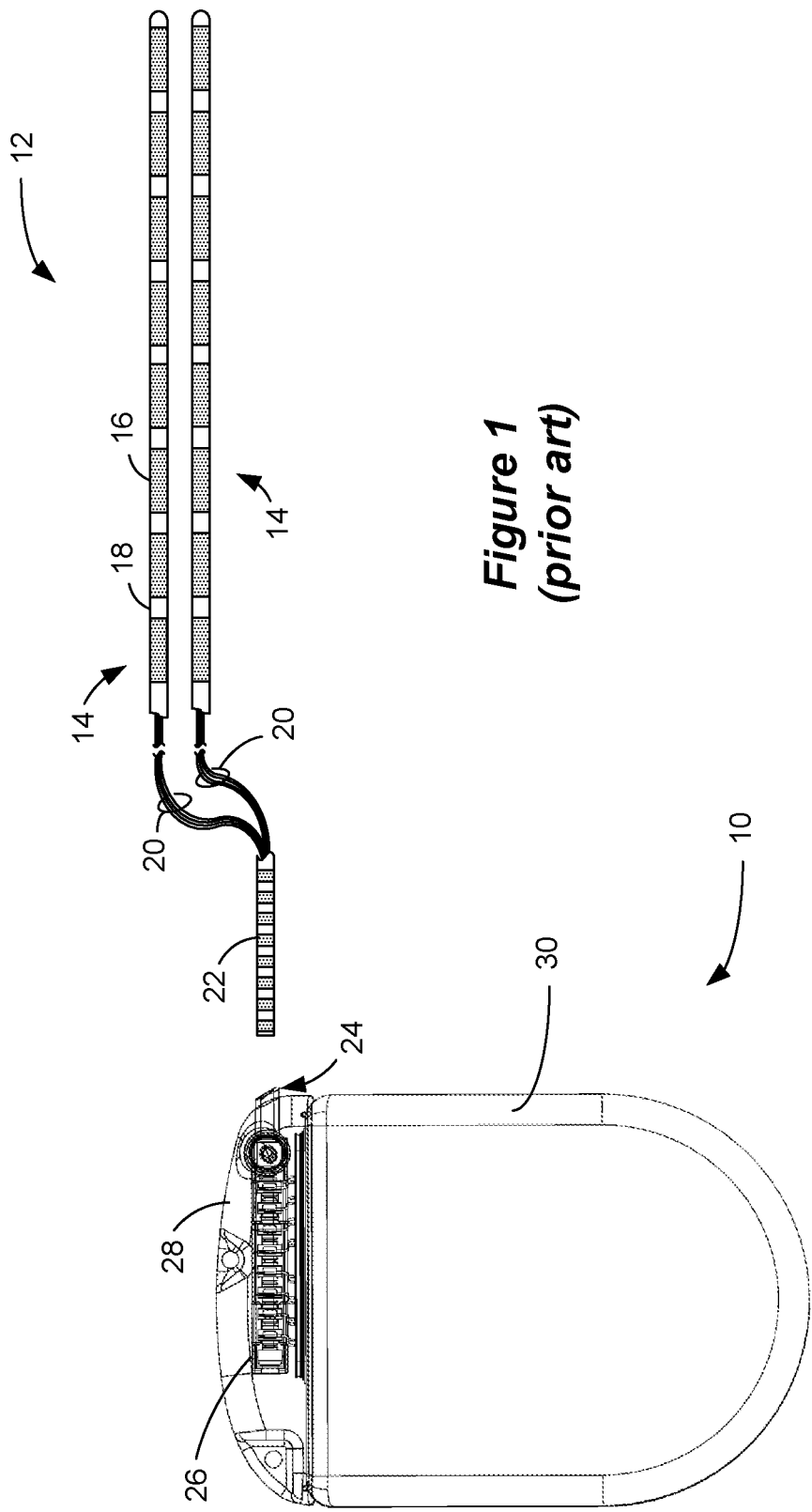
FIG. 1 shows an Implantable Pulse Generator (IPG) and the manner in which electrode leads are affixed to the IPG in accordance with the prior art.
Figure 2:
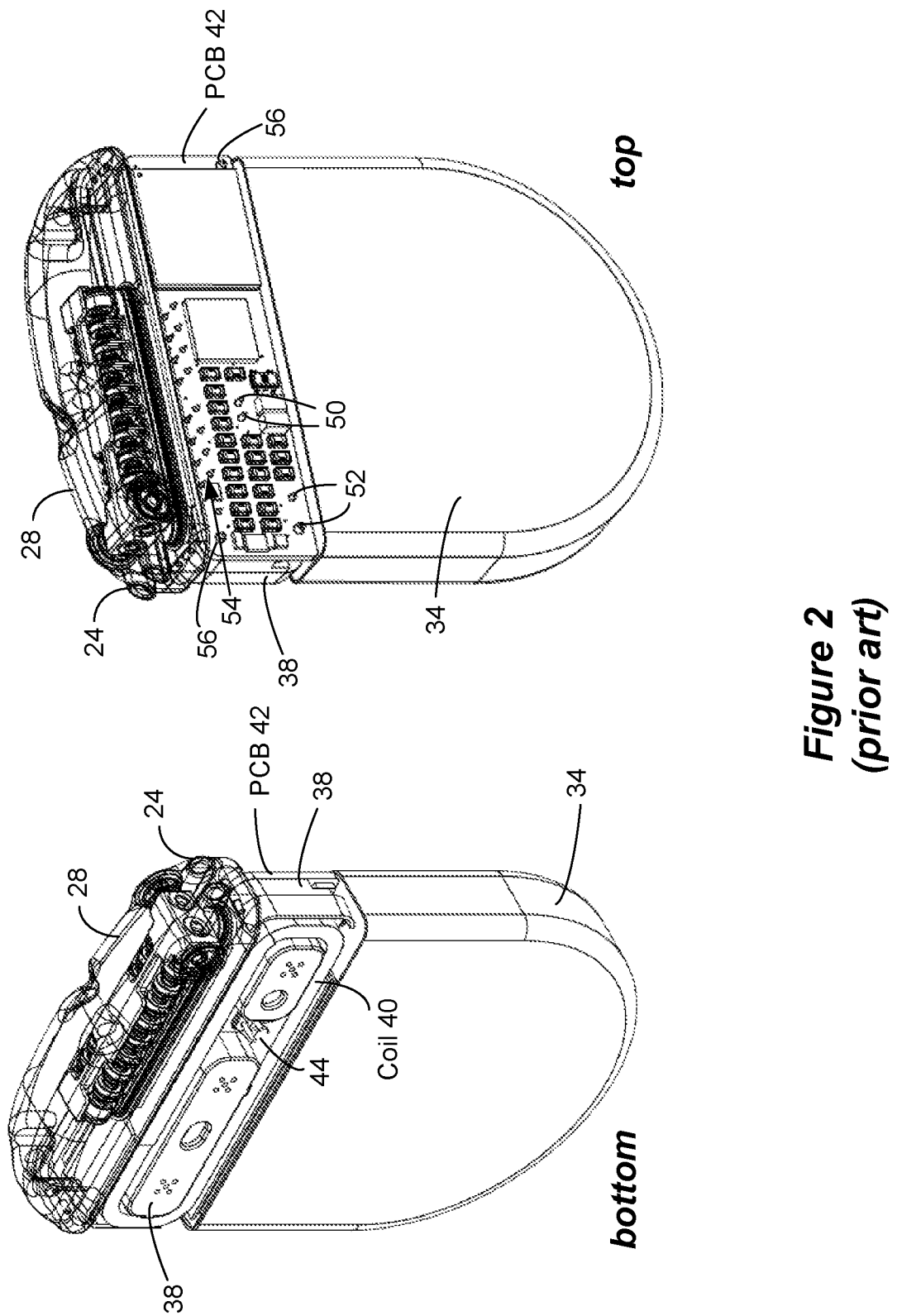
FIG. 2 shows bottom and top views of the IPG with its case removed in accordance with the prior art.
Figure 3:
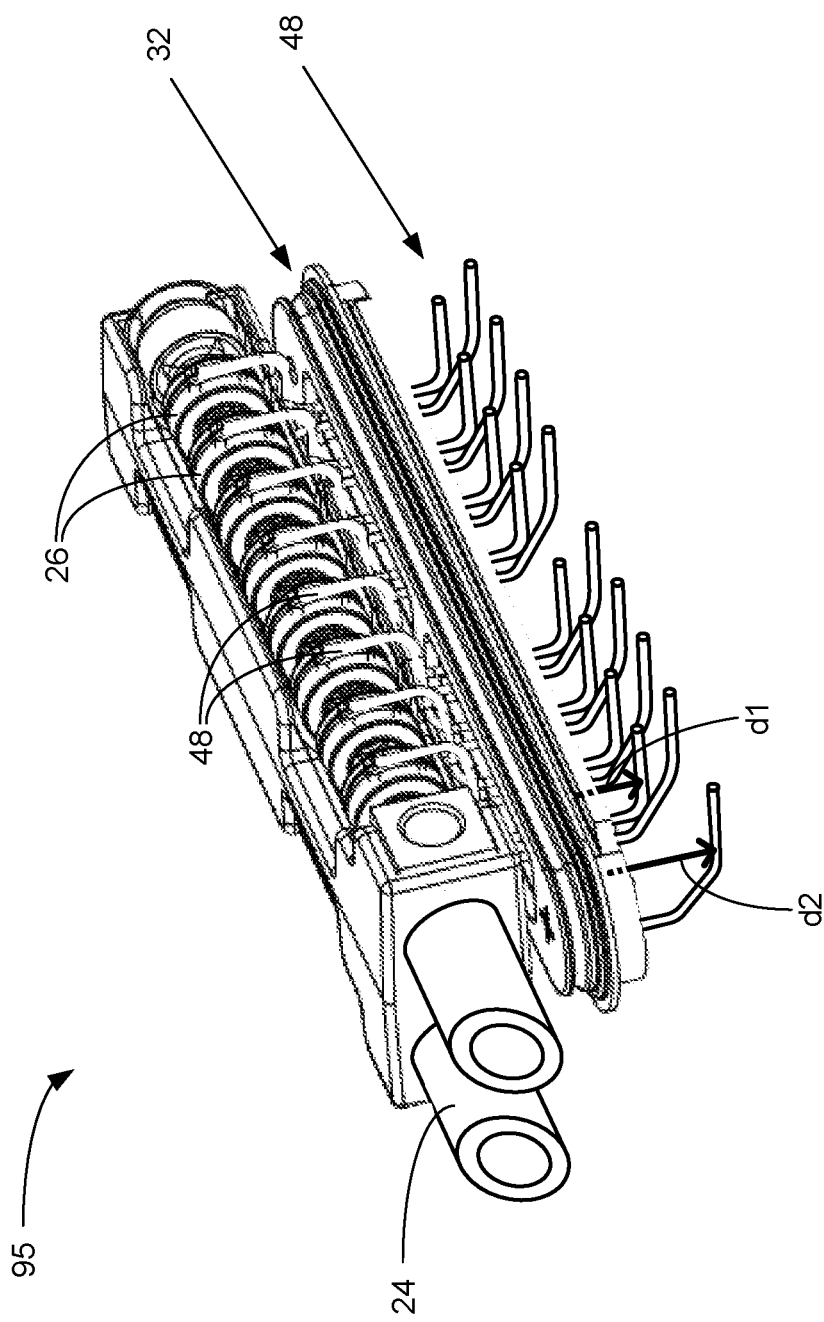
FIG. 3 shows a feedthrough subassembly used in the construction of the IPG in accordance with the prior art.
Figure 8:
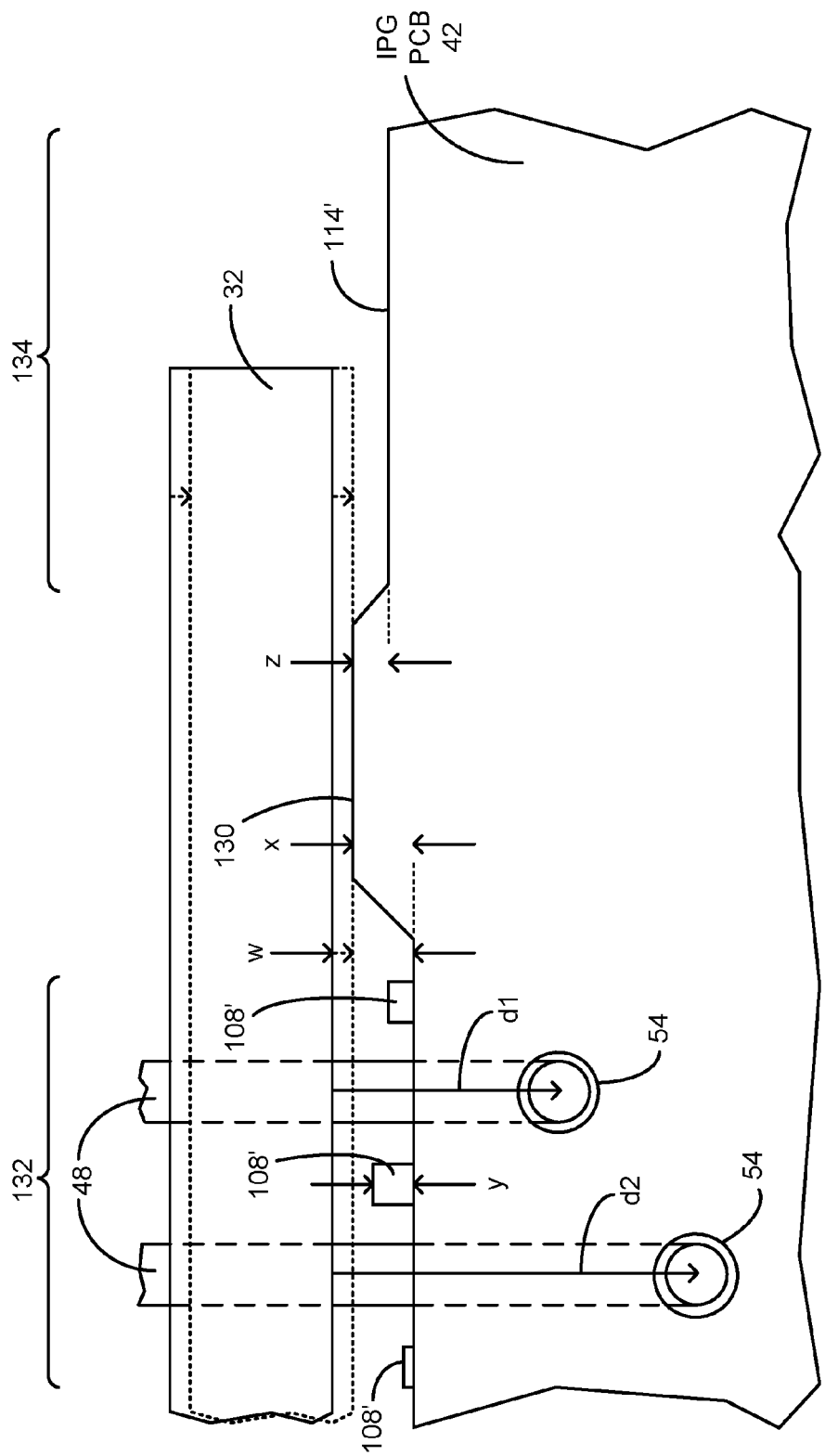

The operation of PCB tab(s) 130 are shown in further detail in the magnified view of FIG. 8. Ideally, the feedthrough 32 would normally reside at a certain distance, w, from the portion 132 of the severed edge 114' between the two tabs 130 (only one shown). However, this distance w is difficult to guarantee because it is affected by manufacturing tolerances, such as the distances d1 and d2 between the bent feedthrough pins 48 and the bottom surface of the feedthrough 32 (see FIG. 3). Such distances d1 and/or d2 may be shorter or longer depending on where the feedthrough pins 48 are bent, and can vary if the angle to which they are bent is not reliably constant. As a result, d1 and/or d2 can vary, and thus when the bent feedthrough pins 48 are placed through feedthrough pin solder holes 54 during IPG 10 assembly, the distance w can likewise vary. Should distance w be unusually small for a given IPG 10, and should a length y of a severed trace 108' be usually long, there is a risk that that trace 108' would short to the feedthrough 32.

PCB tab(s) 130 prevent this from occurring. Notice that the PCB tabs 130 extend perpendicularly from the severed edge 114' by an offset distance of x, which distance x is designed to be larger than a longest expect length y of any severed trace 108' or unwanted particulate. This recesses the severed traces 108', and guarantees that the distance w between the severed traces 108' and the feedthrough 32 will never be smaller than x, and thus w will always be greater than y. As a result, no severed trace 108' can touch the feedthrough 32. Distance x in one example is 0.005 inches (5 mils).

If d1 and/or d2 are unusually large, the natural resting position of the feedthrough 32 relative to the IPG PCB 42 may be such that the feedthrough 32 does not touch the surface of the PCB tab(s) 130. In other words, w would be bigger than x, and a gap may exist between the feedthrough 32 and the top of the PCB tab(s) 130 as shown, which condition does not raise the risk of shorting the severed traces 108'. However, if d1 and/or d2 are unusually small, the feedthrough 32 would contact the top of the PCB tab(s) 130, thus limiting w to x. If w is naturally small by virtue of how the feedthrough pins 48 are bent, offset distance x may force the ends of the feedthrough pins 48 to bend in the feedthrough pin solder holes 54 from their otherwise natural resting positions, but this is not problematic. In effect, PCB tab(s) 130 force an air gap inside of the IPG case 30 to exist between the severed traces 108' and the feedthrough 32, which prevents their shorting. Thus, PCB tab(s) 130 eliminate the need for additional insulation or spacers at the severed edge 114', and provide a simple and cost-effective solution to isolate severed traces 108'.

As noted earlier, it is preferred that none of the traces 108 passing between the extender PCB 104 and the IPG PCB 42 pass through the portion(s) where the PCB tab(s) 130 will be formed. This is because PCB tab(s) 130 may contact the feedthrough 32 as just noted, and thus any severed traces passing through PCB tab(s) 130 might be shorted. However, traces 108 may pass through the portion 134 outside of the PCB tab(s) 130. As shown in FIG. 8, the offset distance used in such portion 134 (z) may differ from that used in portion 132 between the PCB tab(s) 130 (x), or they may be the same. Because the severed edge 114' may extend significantly beyond the length of the feedthrough 32, such as to the right in FIG. 7, use of a smaller offset distance (z), or indeed no offset distance, can be used, as shorting of severed traces 108' is not a concern in such locations.

Figure 9:
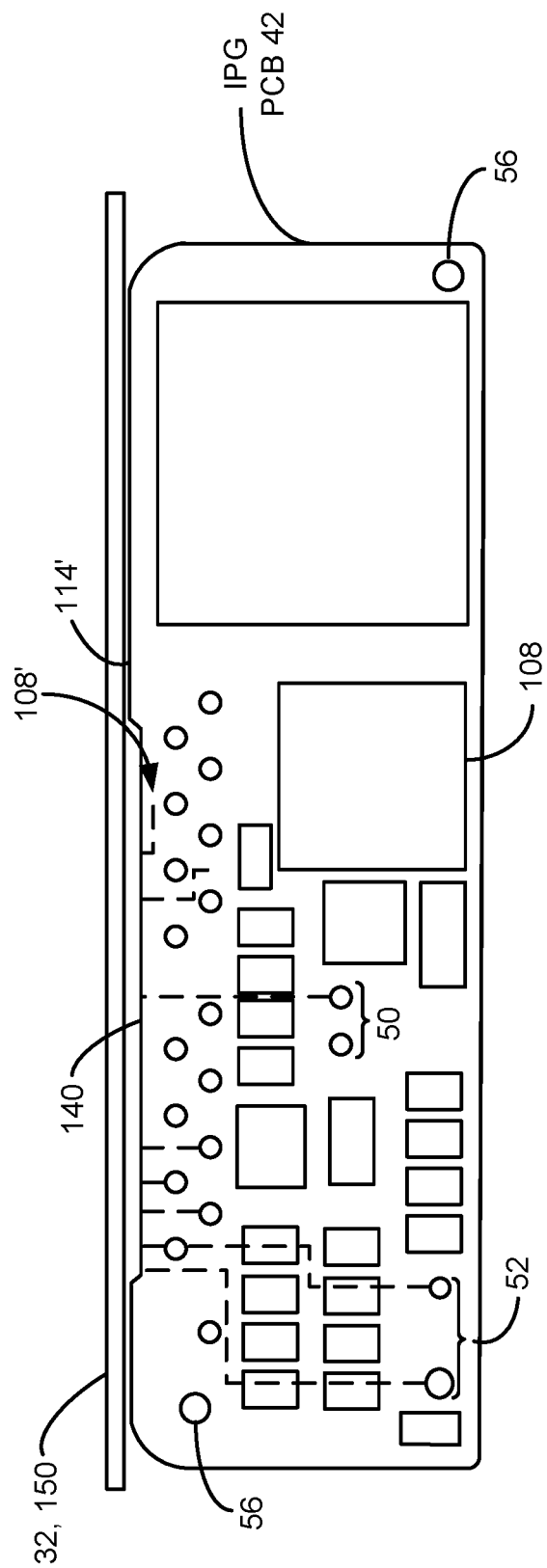
FIG. 9 shows an alternative formation for the IPG PCB having a recess including the severed traces, and shows more generally how such recess prevents shorting of the severed traces to a generic conductive structure.

Other modifications can be made to affect the goal of preventing severed traces from contacting conductive structures in the IPG. For example, in FIG. 9, which shows another example of IPG PCB 42 after it has been singulated from the extender PCB 104 portion of its test PCB 102, the severed edge 114' defines a PCB recess 140 through which all traces 108 pass and are now severed 108'. Because they are recessed by an offset distance (e.g., x) from the rest of the severed edge 114', the severed traces 108' should not be at risk of shorting to the feedthrough 32 to which severed edge 114' is close and may come into contact. Again, more than one recess 140 could be used along severed edge 114'.

It should be noted that while the present invention was contemplated given the particular geometry of the IPG 10 in which the severed edge 114' of the IPG PCB 42 is close to the feedthrough 32, severed edges formed as disclosed herein may run the risk of shorting to any conductive structures 150 in an IPG or other medical device, such as the case 30, another PCB, other electrical components or wires, etc. The PCB tab(s) 130 and/or PCB recess(es) 140 can also be used to prevent shorting of the severed traces 108' to such other conductive structures 150. Indeed, the disclosed techniques can have applicability outside of medical devices.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for constructing and testing a circuit board for an implantable medical device, comprising:
    coupling electronic components to a circuit board, wherein the circuit board comprises an implantable medical device portion and an extender portion, wherein the extender portion comprises a plurality of traces and a connector with a plurality of contacts, wherein each trace is coupled to a node in the implantable medical device portion and to a contact of the connector;
    testing the electronic components via the connector; and
    singulating the implantable medical device portion from the extender portion thereby forming a severed edge comprising the traces as severed,
    wherein the severed edge of the implantable medical device portion comprises at least one first portion comprising at least some of the severed traces, and at least one second portion not comprising the severed traces, wherein the at least one first portion is recessed with respect to the at least one second portion along the severed edge.

2. The method of claim 1, wherein testing the electronic components comprises inserting the connector in a socket of a tester wherein the electronic components are configured to implement the functionality of the implantable medical device.

3. The method of claim 1, wherein at least some of the nodes in the implantable medical device portion comprise electrode nodes each coupleable to an electrode of the implantable medical device.

4. The method of claim 3, wherein the implantable medical device portion comprises a plurality of holes, wherein each hole is connected to one of the electrode nodes and is coupleable to a feedthrough pin coupleable to one of the electrodes.

5. The method of claim 1, wherein the at least one second portion is configured to prevent the severed traces in the at least one first portion from contacting a conductive structure.

6. The method of claim 1, wherein the at least one first portion and the least one second portion are formed during the singulation step by cutting along a sever line defining shapes of the at least one first portion and the least one second portion.

7. The method of claim 1, wherein the at least one second portion comprises two or more tabs.

8. The method of claim 7, wherein each first portion is positioned between a pair of the tabs.

9. The method of claim 1, wherein the extender portion has a larger area than the implantable medical device portion.

10. The method of claim 1, wherein the extender portion does not have any electronic devices mounted to it.

11. A method for constructing a circuit board for an implantable medical device, comprising:
    forming a test circuit board by coupling electronic components to an implantable medical device portion of the test circuit board and routing electrical traces between nodes in the implantable medical device portion and contacts in a connector in an extender portion of the test circuit board; and
    singulating the implantable medical device portion from the extender portion, wherein a severed edge of the implantable medical device portion comprises:
        one or more second portions that do not comprise severed traces, and one or more first portions comprising at least one severed trace, wherein the one or more first portions are recessed with respect to the one or more second portions.

12. The method of claim 11, wherein the contacts have a size and pitch to meet with corresponding test contacts in a socket of a test system.

13. The method of claim 12, further comprising:
inserting the connector into the socket; and
testing functionality of at least some of the electronic components.

14. The method of claim 11, wherein the extender portion has an area that is at least two times as large as an area of the implantable medical device portion.

15. The method of claim 11, wherein at least some of the nodes in the implantable medical device portion comprise electrode nodes each coupleable to an electrode of the implantable medical device.

16. The method of claim 11, wherein one or more second portions are configured to prevent the at least one severed trace in the one or more first portions from contacting a conductive structure.

17. The method of claim 11, wherein the one or more first portions and the one or more second portions are formed during the singulation step by cutting along a sever line.

18. The method of claim 11, wherein the one or more second portions comprise two or more tabs.

19. The method of claim 18, wherein each first portion is positioned between a pair of the tabs.

20. The method of claim 11, wherein the electrical traces are arranged in two layers.

* * * * *